(12) United States Patent
Morita et al.

(10) Patent No.: US 8,263,123 B2
(45) Date of Patent: Sep. 11, 2012

(54) RAPIDLY DISINTEGRATING TABLET CONTAINING POLYVINYL ALCOHOL

(75) Inventors: Yutaka Morita, Saitama (JP); Masanobu Yasui, Saitama (JP); Takayuki Ohwaki, Saitama (JP); Yuki Tsushima, Saitama (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 601 days.

(21) Appl. No.: 11/778,504

(22) Filed: Jul. 16, 2007

(65) Prior Publication Data

US 2008/0014262 A1    Jan. 17, 2008

Related U.S. Application Data

(62) Division of application No. 10/203,687, filed as application No. PCT/JP01/01575 on Mar. 1, 2001, now Pat. No. 7,727,548.

(30) Foreign Application Priority Data

Mar. 1, 2000  (JP) .................................. 2000-56176

(51) Int. Cl.
*A61Q 9/20*  (2006.01)
(52) U.S. Cl. ........................ 424/465; 424/464
(58) Field of Classification Search .................. None
See application file for complete search history.

(56) References Cited

U.S. PATENT DOCUMENTS

| | | | |
|---|---|---|---|
| 4,725,440 A | 2/1988 | Ridgway et al. | |
| 5,013,557 A | 5/1991 | Tai | |
| 5,077,053 A | 12/1991 | Kuncewitch et al. | |
| 5,084,278 A | 1/1992 | Mehta | |
| 5,286,489 A | 2/1994 | Tsau et al. | |
| 5,288,501 A | 2/1994 | Nürnberg et al. | |
| 5,464,612 A | 11/1995 | Matoba et al. | |
| 5,466,464 A | 11/1995 | Masaki et al. | |
| 5,489,436 A | 2/1996 | Hoy et al. | |
| 5,576,014 A | 11/1996 | Mizumoto et al. | |
| 5,612,026 A | 3/1997 | Diehl | |
| 5,656,284 A | 8/1997 | Balkin | |
| 5,763,449 A | 6/1998 | Anaebonam et al. | |
| 5,827,507 A | 10/1998 | Oshima et al. | |
| 5,874,074 A | 2/1999 | Smith | |
| 5,955,106 A | 9/1999 | Moeckel et al. | |
| 5,962,535 A | 10/1999 | Miyamoto et al. | |
| 6,214,386 B1 | 4/2001 | Santus et al. | |
| 6,368,625 B1 * | 4/2002 | Siebert et al. ............... | 424/466 |
| 6,455,053 B1 | 9/2002 | Okada et al. | |
| 6,576,677 B1 | 6/2003 | Ukai et al. | |
| 6,586,004 B2 | 7/2003 | Shimizu et al. | |
| 6,656,492 B2 | 12/2003 | Kajiyama et al. | |
| 6,743,443 B1 * | 6/2004 | Furitsu et al. ............... | 424/465 |
| 7,727,548 B2 * | 6/2010 | Morita et al. ............... | 424/465 |

FOREIGN PATENT DOCUMENTS

| | | |
|---|---|---|
| EP | 0590963 | 4/1994 |
| EP | 0691122 | 1/1996 |
| EP | 0748628 | 12/1996 |
| EP | 0753296 | 1/1997 |
| EP | 0 922 464 | 6/1999 |
| EP | 1 120 120 A1 | 8/2000 |
| GB | 2081092 | 2/1982 |
| JP | 51-76413 | 7/1976 |
| JP | 54-76818 | 6/1979 |
| JP | 60-204712 A | 10/1985 |
| JP | 61-130239 A | 6/1986 |
| JP | 03-005418 A | 1/1991 |
| JP | 4-282312 A | 10/1991 |
| JP | 03-287535 A | 12/1991 |
| JP | 04-018015 A | 1/1992 |
| JP | 4-235136 A | 8/1992 |
| JP | 4-262758 A | 9/1992 |
| JP | 4-346937 A | 12/1992 |
| JP | 5-163154 A | 6/1993 |
| JP | 5271054 | 10/1993 |
| JP | 6218028 | 8/1994 |
| JP | 07-267850 A | 10/1995 |
| JP | 819589 | 1/1996 |
| JP | 8-333245 A | 12/1996 |
| JP | 948726 | 2/1997 |
| JP | 9-143100 | 6/1997 |
| JP | 09-143100 A | 6/1997 |
| JP | 10-0036292 A | 2/1998 |
| JP | 10/114683 A | 5/1998 |
| JP | 2807346 | 7/1998 |
| JP | 41-1106353 | 4/1999 |
| JP | 11199517 | 7/1999 |
| JP | 11-228450 A | 8/1999 |
| JP | 2005-41887 A | 2/2005 |
| WO | WO 98/53798 | * 12/1998 |
| WO | WO-9918936 | 4/1999 |
| WO | WO-00/20033 | 4/2000 |
| WO | WO-00/25754 | 5/2000 |

OTHER PUBLICATIONS

Drug Information on Vantin® by Pharmacia/& Upjohn, obtained through on-line PDR (revised Nov. 2000).

(Continued)

*Primary Examiner* — Jyothsna Venkat
(74) *Attorney, Agent, or Firm* — Birch, Stewart, Kolasch & Birch, LLP

(57) ABSTRACT

The present invention provides a quickly disintegrating tablet which has quick disintegrability and solubility in an oral cavity, and does not have uncomfortable tastes such as bitterness, has a small variation of a tablet physical property even in storage under a humidifying condition, and has substantially no change in a medicine content in the tablet and tablet appearance and which is superior in stability; and a manufacturing method of the tablet. That is, it provides: a quickly disintegrating tablet which is prepared by blending a medicine with a saccharide and polyvinyl alcohol, which has small variations of tablet weight, tablet hardness, tablet diameter and tablet thickness, and which is superior in medicine stability in the tablet; and a manufacturing method of the tablet.

3 Claims, No Drawings

OTHER PUBLICATIONS

US Office Action issued in U.S. Appl. No. 09/380,310 dated Nov. 13, 2000.
US Office Action issued in U.S. Appl. No. 09/380,310 dated Jul. 3, 2001.
US Office Action issued in U.S. Appl. No. 09/380,310 dated Mar. 27, 2002.
US Office Action issued in U.S. Appl. No. 09/380,310 dated Oct. 25, 2002.
US Office Action issued in U.S. Appl. No. 09/380,310 dated Jan. 27, 2004.
US Office Action issued in U.S. Appl. No. 09/380,310 dated Oct. 21, 2004.
US Office Action issued in U.S. Appl. No. 09/380,310 dated Jul. 29, 2005.
US Office Action issued in U.S. Appl. No. 09/380,310 dated Jun. 2, 2006.
US Office Action issued in U.S. Appl. No. 09/380,310 dated Feb. 26, 2007.
US Office Action issued in U.S. Appl. No. 09/380,310 dated Sep. 28, 2007.
US Office Action issued in U.S. Appl. No. 09/380,310 dated Mar. 17, 2008.
US Office Action issued in U.S. Appl. No. 09/380,310 dated Dec. 29, 2008.
Supplementary Search Report issued on Jan. 27, 2006, in connection with European Patent Application No. 01 908 204.9-2123.
Official European Patent Office Communication dated Sep. 13, 2006, issued in connection with European Patent Application No. 01 908 402.9-2123.
Applicant's Response dated Mar. 19, 2007, in response to Official Communication issued on Sep. 13, 2006, in connection with European Patent Application No. 01 908 204.9-2123.
Official European Patent Office Communication dated Oct. 17, 2008, issued in connection with European Patent Application No. 01 908 204.9-2123.
Applicant's Response dated Jan. 23, 2009, in response to Official Communication issued on Oct. 17, 2008, in connection with European Patent Application No. 01 908 204.9-2123.
Notice of Acceptance issued Feb. 20, 2009, in connection with European Patent Application No. 01 908 204.9-2123.
US Office Action issued in U.S. Appl. No. 10/203,687 dated Oct. 20, 2004.
US Office Action issued in U.S. Appl. No. 10/203,687 dated Jul. 13, 2005.
US Office Action issued in U.S. Appl. No. 10/203,687 dated Mar. 6, 2006.
US Office Action issued in U.S. Appl. No. 10/203,687 dated Jan. 16, 2007.
US Office Action issued in U.S. Appl. No. 10/203,687 dated Nov. 30, 2007.
US Office Action issued in OA U.S. Appl. No. 10/203,687 dated Aug. 15, 2008.
Office Action issued Oct. 1, 2009, in Georgian Application No. 87447 (with translation).
1998 *Physician Desk Reference*, p. 1203.
Wade and Weller-Editors: *Handbook of Pharmaceutical Excipients, Povidone*, p. 392, 1994.
*Research Disclosure* 176019 (Derwent WPI Acc No. 78-92367 A/51) (1978).
Drug Information for Vantin, *Physician's Desk Reference*—1995.
Y. Kawakami et al., *J. Bioorganic & Med, Chem. Lett.*, 1996, vol. 4, (1429-1446).

\* cited by examiner

RAPIDLY DISINTEGRATING TABLET CONTAINING POLYVINYL ALCOHOL

This application is a Divisional Application of application Ser. No. 10/203,687 filed on Aug. 13, 2002, now U.S. Pat. No. 7,727,548 which is the national phase application under 35 U.S.C. §371 of PCT International Application No. PCT/JP01/01575 which has an International filing date of Mar. 1, 2001, which designated the United States of America and claims priority from Japanese Application No. 2000-56176 filed Mar. 1, 2000.

TECHNICAL FIELD

The present relates to a quickly disintegrating tablet which is prepared by blending a medicine with a saccharide and polyvinyl alcohol, has small variations of tablet weight, tablet hardness, tablet diameter and tablet thickness and is superior in medicine stability in the tablet, and to a method for producing the tablet.

PRIOR ART

Various preparations have been known as quickly disintegrating tablets, and particularly an intraoral quickly disintegrating tablet which is quickly disintegrated in an oral cavity after taken has been noted in recent years. Since the intraoral quickly disintegrating tablet can be easily taken without water, they are recently receiving public attention as a dosage form which is suitable for the people having insufficient swallowing functions such as aged people and small children.

It has been known that the intraoral quickly disintegrating tablets can be prepared, for example, by the use of wet powder. With regard to a method where wet powder is dried without a tableting step whereupon the intraoral quickly disintegrating tablets are prepared, there is disclosed for example in Application No. 5-511543 (corresponding to WO 99/12769) for a "solid preparation which is quickly disintegrated in the mouth comprising an active ingredient, a saccharide selected from lactose and/or mannitol and agar".

On the other hand, with regard to an intraoral quickly disintegrating tablet prepared by a compression-molding of wet powder filled in a molding machine, there are disclosed, for example, "a method for the manufacture of an intraoral quickly disintegrating tablet where a mixture containing a pharmaceutical ingredient, a saccharide and water which is in an amount of moisturizing the particle surface of the saccharide is made into a tablet" in JP-A 5-271054; "an intraoral quickly disintegrating tablet comprising a pharmaceutical agent, a saccharide, a sugar alcohol and a water-soluble polymer and being prepared by moisturizing and molding" in JP-A 9-48726; and a "wet-process tablet where a pharmaceutical agent is mixed with a saccharide, a filler, etc., kneaded after addition of water and/or organic solvent, filled in a mold and subjected to a compression-molding and a method for manufacturing the same" in JP-A 6-218028. Further, with regard to a method for the molding of an intraoral quickly disintegrating tablet, there is disclosed in JP-A 8-19589 for an invention concerning "a method for the manufacture of a tablet where wet powder is filled in a hole for molding the tablet and at least one side of the wet powder in the hole is made into a shape of a tablet by means of a metal mold for molding with a film for prevention of adhesion and an apparatus for manufacturing the tablet".

However, such quickly disintegrating tablet is functionally designed so as to be quickly disintegrated with a small amount of water or saliva in a mouth, and therefore has large hygroscopicity. Particularly in storage under a humidifying condition, a tablet diameter and tablet thickness are expanded and tablet hardness largely varies by an absorbed moisture. Additionally, decomposition promotion of the medicine in the tablet and change of tablet appearance easily occur.

Therefore, there have been much waited for developments: of a physicochemically stable quickly disintegrating tablet including a medicine, that is, a stable oral drug product which is easy for aged people to take, whose taste or feeling during taking is good, which can be taken even by an adult having a swallowing capability without water, and of a method for producing the tablet. Concretely, for example, there have been waited for: a quickly disintegrating tablet which has a quick disintegrability and solubility in an oral cavity, has no uncomfortable tastes such as bitterness, has small variations of tablet weight, tablet hardness, tablet diameter and tablet thickness even in storage under a humidifying condition, has substantially no change of a medicine content in the tablet and tablet appearance, and is superior in stability; and for a method for producing the tablet.

DISCLOSURE OF THE INVENTION

Under such circumstances, the present inventors have carried out an intensive study for investigating quickly disintegrating tablet with an excellent physicochemical stability containing medicament and a saccharide, and a method for manufacturing the tablet. As a result, it has been found that the aimed object can be achieved by the constitutions as mentioned below whereupon the present invention has been accomplished.

The present invention is a quickly disintegrating tablet which is prepared by blending a medicine with a saccharide and polyvinyl alcohol, which has small variations of tablet weight, tablet hardness, tablet diameter and tablet thickness, and which is superior in medicine stability in the tablet.

Moreover, the present invention provides a quickly disintegrating tablet comprising a medicine, saccharide and polyvinyl alcohol.

According to the present invention, there is also provided a manufacturing method of a quickly disintegrating tablet which is manufactured by mixing a medicine with a saccharide, kneading the mixture with water including polyvinyl alcohol dissolved therein or an aqueous organic solvent, and subjecting to a compression-molding, which has small variations of tablet weight, tablet hardness, tablet diameter and tablet thickness, and which is superior in medicine stability in the tablet.

Furthermore, according to the present invention, there is provided a manufacturing method of a quickly disintegrating tablet which is prepared by mixing a medicine with a saccharide, kneading the mixture with water including polyvinyl alcohol dissolved therein or an aqueous organic solvent, filling a mold with the mixture, and subjecting it to a compression-molding via a film, which has small variations of tablet weight, tablet hardness, tablet diameter and tablet thickness, and which is superior in medicine stability in the tablet.

The medicine is preferably famotidine, midodrine hydrochloride, brotizolam or donepezil hydrochloride.

The saccharide is preferably at least one selected from mannitol, lactose, saccharose, trehalose, xylitol and erythritol.

The compounding ratio of the saccharide is 0.8 part by weight or more to one part by weight of the tablet, the compounding ratio of polyvinyl alcohol is 0.0001 to 0.1 part by weight to one part by weight of the tablet, and the compounding ratio of the medicine is preferably a pharmacologically effective amount.

The quickly disintegrating tablet according to the present invention is a tablet which is quickly disintegrated with a small amount of water or saliva in a mouth, and examples of the tablet include an intraoral quickly disintegrating tablet. The intraoral quickly disintegrating tablet can easily be taken without water, and is a tablet quickly disintegrated in an oral cavity after taken.

Since "the quickly disintegrating tablet containing the medicine blended with the saccharide and polyvinyl alcohol" according to the present invention is surprisingly small in moisture-absorption characteristics as compared with a conventional quickly disintegrating tablet, variations of tablet weight, tablet hardness, tablet diameter and tablet thickness are small, and the medicine content in the tablet and tablet appearance hardly change especially in storage under a humidifying condition, and the tablet has remarkably superior characteristics such as superior medicine stability.

Examples of the medicine in the present invention include famotidine, midodrine hydrochloride, brotizolam, donepezil hydrochloride, etizolam, glibenclamide, chlormadinone acetate, triazolam, ambroxol hydrochloride, atenolol, sodium picosulfate, sennoside, azulene glutamate, sodium valproate, furosemide, isosorbide dinitrate, bromperidol, ketotifen fumarate, domperidone, captopril, loperamide hydrochloride, enalapril maleate, simbastatin, loxoprofen sodium, amezinium methylsulfate, nicergoline, bromocriptine mesylate, cimetidine, oxybutynin hydrochloride, ticlopidine hydrochloride, diclofenac sodium, doxazosin hydrochloride, pranoprofen, carbamazepine, nicardipine hydrochloride, nifedipine, haloperidol, ampiroxicam, droxidopa, dantrolene sodium, pimobendan, aprindine hydrochloride, pilsicainide hydrochloride, pirmenol hydrochloride, mexiletine hydrochloride, carteolol hydrochloride, barnidipine hydrochloride, propranolol hydrochloride, ditiazem hydrochloride, dipyridamole, cytochrome C, danazol, tamsulosin hydrochloride, dihydrotachysterol, etretinate, alfacarcidol, calcitriol, ethyl eicosapentaenoate, propagermanium, trientine hydrochloride, D-penicillamine, cyclosporine, tacrolimus hydrate, ibudirast, tazanolast, tranilast, emedastin fumarate, pranlukasto hydrate, kanamycin sulfate, colistin methane sulfonate, ceftibuten, talampicillin hydrochloride, cyclacillin, cefatrizine propylene, cefixime, cefdinir, fosfomycin calcium, cycloserine, rifampicin, lomefloxacin hydrochloride, cinoxacin, itraconazole and fluconazole. However, the medicine for use in the present invention is not limited to these compounds.

As the saccharide in the present invention, any one is acceptable, so long as it is water-soluble and stable, For example, mannitol, lactose, sucrose, trehalose, xylitol and erythritol may be proposed. In the present invention, they can be used singly or in a combination of two or more thereof.

Moreover, the compounding ratio of the saccharide in the quickly disintegrating tablet in the present invention differs with the type of the medicine to be blended, but is generally 0.8 part by weight or more, preferably 0.85 part by weight or more, more preferably 0.9 part by weight or more to one part by weight of the tablet.

A blending method of the saccharide in the present invention is not particularly limited. That is, the method may comprise the steps of: mixing a medicine with all saccharides; kneading the mixture with water including polyvinyl alcohol dissolved therein or an aqueous organic solvent as it is; filling a mold with the mixture; and subjecting it to a compression-molding via a film, or may comprise the steps of: mixing a medicine with some of saccharides and granulating and drying the mixture; further additionally mixing the granulated powder with the saccharides; kneading the powder with water including polyvinyl alcohol dissolved therein or an aqueous organic solvent; filling a mold with the mixture; and subjecting it to a compression-molding via a film.

Polyvinyl alcohol in the present invention has a function of a binder in many cases, but may be used as a usual filler. A compounding ratio of polyvinyl alcohol in the present invention is in generally 0.0001 to 0.1 part by weight, preferably 0.001 to 0.05 part by weight to one part by weight of the tablet, and can appropriately be increased or decreased so that desired disintegrability or hardness is obtained. Additionally, polyvinyl alcohol may be added as a powder to the mixture of the medicine and saccharide, or may be added to dissolve in an organic solvent, pure water or aqueous organic solvent.

To the quickly disintegrating tablet of the present invention, there can be added, if necessary, a filler, a lubricant, a disintegrant, a sweetening agent, a refrigerant and/or a coloring agent which are usually used, in addition to the saccharide and polyvinyl alcohol. Furthermore, the quickly disintegrating tablet according to the present invention can be prepared by mixing the medicine with the saccharide and polyvinyl alcohol; if necessary, adding the usually usable filler, lubricant, disintegrant, sweetening agent, refrigerant and/or coloring agent thereto; kneading with water or an aqueous organic solvent; filling in a mold; and subjecting to a compression-molding.

Examples of the organic solvent or the organic solvent for use in the aqueous organic solvent according to the present invention include ethanol, propanol, isopropanol, etc., but ethanol is preferable. Moreover, the aqueous organic solvent is a mixture solution of water and organic solvent, and the compounding ratio can freely be selected. The compounding ratio of the organic solvent in the aqueous organic solvent is generally 0.05 to 0.99 part by weight, preferably 0.2 to 0.98 part by weight, more preferably 0.25 to 0.98 part by weight to one part by weight of the aqueous organic solvent.

The kneading and granulating operations carried out by adding an auxiliary agent for making the preparation and a solvent may be conducted using the conventionally used apparatus. For example, a fluidized bed granulator, a tumbling granulator and an extrusion granulator may be used.

Examples of the filler include crystalline cellulose, ethyl cellulose, dextrin, various types of cyclodextrin (α-cyclodextrin, β-cyclodextrin, γ-cyclodextrin) and derivatives thereof, and pullulan. Examples of the disintegrant include light silicic anhydride, crystalline cellulose, cross povidone, lowly substituted hydroxypropyl cellulose, cross carmellose sodium, calcium silicate, magnesium metasilicate aluminate, carboxymethylcellulose, carboxymethylcellulose calcium, hydroxylpropyl starch, carboxymethyl starch sodium, partially α-alpha starch, sodium alginate and cornstarch. Examples of the lubricant include magnesium stearate, calcium stearate, stearic acid, talc, and sodium fumarate stearate. Examples of the coloring agent include yellow iron sesquioxide, yellow iron oxide, Yellow #4 dye for food, Yellow #5 dye for food, Yellow #4 dye for food aluminum lake, red iron oxide, iron sesquioxide, Red #2 dye for food, Red #3 dye for food and Red #102 dye for food. Examples of the refrigerant include 1-menthol and mentha water, and examples of the sweetening agent include aspartame, stevia extract, glycyrrhiza, saccharine, saccharine sodium, and dipotassium glycyrrhizinate.

In the present invention, these can be used singly or in a combination of two or more thereof.

In the molding of the wet powder containing the medicine, saccharide and polyvinyl alcohol, a lubricant may be applied, if necessary, on upper and lower sides of the kneaded mixture filled therein whereby an adhesion during the compressing step can be prevented but, for the manufacture in a more efficient and easier manner, it is preferred to use a tablet manufacturing apparatus which is disclosed in JP-A 8-19589. Thus, a wet powder is filled in a mold for the tablet molding of the tablet manufacturing apparatus and at least one surface of the wet powder in the mold is molded via an adhesion-preventing film whereby an adhesion of the wet powder to the metal mold for molding can be prevented and a quickly disintegrating tablets are able to be manufactured in an efficient manner.

The pressure applied upon the compression-molding of the web powder after kneading the mixture or upon tableting via an adhesion-preventing film after filling in a mold in the present invention is generally 2 to 150 kg/cm$^2$, preferably 2 to 100 kg/cm$^2$, more preferably 3 to 50 kg/cm$^2$.

The drying temperature after the compression-molding or the tableting in the present invention is not particularly limited, and usually 15-90° C.

The tablet hardness of the quickly disintegrating tablet prepared by the manufacturing method in accordance with the present invention is usually 1-15 kg, preferably 1.5-10 kg, more preferably, 2-10 kg. Time for disintegration of the quickly disintegrating tablet is usually 0.05-2 minutes, preferably 0.05-0.5 minute, more preferably 0.05-0.3 minute.

The water content in the wet powder which is kneaded in the present invention is 0.01-25% by weight, preferably 0.1-20% by weight or, more preferably, 0.1-15% by weight of the kneaded mixture.

The quickly disintegrating tablet according to the present invention can be manufactured, for example, as follows. For example, 20 g of famotidine and 189 g of mannitol are sufficiently mixed in a mixer. To the mixture was added a 55% aqueous ethanol solution in which 1 g of polyvinyl alcohol was dissolved, followed by kneading for about five minutes. Subsequently, the tablet manufacturing apparatus disclosed in the JP-A 8-19589 is used to charge the kneaded material into the mold, and the material is subjected to a compression-molding via a film with a pestle having a diameter of 8 mm at a compression pressure of 35 kg/cm$^2$. The molded material is dried for about three hours at 60° C. in a drier, to give the quickly disintegrating tablet containing 20 mg of famotidine in one tablet (210 mg).

According to the present invention, it is possible to manufacture the quickly disintegrating tablet which has small moisture-absorption characteristics under a humidifying storage condition, and which is superior in the chemical stability of the medicine. That is, it is possible to manufacture the quickly disintegrating tablet in which variations of tablet weight, tablet hardness, tablet diameter and tablet thickness are small even in the storage under the humidifying condition, and has substantially no change in the medicine content in the tablet and the tablet appearance and which is superior in stability. Effect examples will be described hereinafter.

EXPERIMENTAL EXAMPLE

Satisfactory Tablet Characteristics of Quickly Disintegrating Tablet Blended with Polyvinyl Alcohol According to the Present Invention "Quickly disintegrating tablets of medicines blended with saccharides and polyvinyl alcohol as a binder" obtained in Examples 1, 2 and 3 described hereinafter were compared with "quickly disintegrating tablets of medicines blended with saccharides and polyvinyl pyrrolidone as the binder" obtained in Reference Examples 1, 2, 3 and physical properties were evaluated. Additionally, as the medicine, midodrine hydrochloride is blended in Example 1 and Reference Example 1, brotizolam is blended in Example 2 and Reference Example 2, and famotidine is blended in Example 2 and Reference Example 2, and drug products of Reference Examples 1, 2, 3 were manufactured in methods similar to those of drug products of Examples 1, 2, 3 and by changing only the type of the binder.

The physical properties were evaluated by measuring the tablet weight, tablet hardness, tablet diameter, and tablet thickness according to Japanese Pharmacopoeia after each product was stored for two weeks under eight conditions (0 to 94%) of relative humidity at 25° C. Additionally, a tablet weight increase ratio of the tablet stored for two weeks under each condition was obtained by the following equation.

$$\text{the weight increase ratio}(\%) = \frac{\text{weight of the tablet stored for two weeks} - \text{initial tablet weight before the storage}}{\text{initial tablet weight before the storage}} \times 100$$

Prescriptions are shown in Table 1. Moreover, the results of the physical property evaluation of the quickly disintegrating tablets containing midodrine hydrochloride, brotizolam and famotidine are shown in Tables 2, 3 and 4, respectively.

TABLE 1

|  | Example | | | Reference Example | | |
| --- | --- | --- | --- | --- | --- | --- |
| Prescription | 1 | 2 | 3 | 1 | 2 | 3 |
| midodrine hydrochloride | 2.00 | — | — | 2.00 | — | — |
| brotizolam | — | 0.25 | — | — | 0.25 | — |
| famotidine | — | — | 20.00 | — | — | 20.00 |
| mannitol | 171.78 | 173.53 | 188.53 | 171.25 | 173.00 | 187.90 |
| polyvinyl alcohol | 1.22 | 1.22 | 1.47 | — | — | — |
| polyvinylpyrrolidone | — | — | — | 1.75 | 1.75 | 2.10 |
| Total | 175 | 175 | 210 | 175 | 175 | 210 |

Unit: mg

TABLE 2

| Relative Humidity (%) | weight increase ratio (%) Ex. 1 | weight increase ratio (%) Ref Ex. 1 | Hardness (kg) Ex. 1 | Hardness (kg) Ref Ex. 1 | diameter (mm) Ex. 1 | diameter (mm) Ref Ex. 1 | thickness (mm) Ex. 1 | thickness (mm) Ref Ex. 1 |
|---|---|---|---|---|---|---|---|---|
| 0  | 0.06 | −0.04 | 5.6  | 6.2  | 8.00 | 7.99 | 3.55 | 3.48 |
| 31 | 0.11 | −0.06 | 5.7  | 5.5  | 8.00 | 7.99 | 3.53 | 3.53 |
| 40 | 0.02 | 0.02  | 5.5  | 5.5  | 8.00 | 8.00 | 3.54 | 3.54 |
| 53 | 0.11 | 0.08  | 5.2  | 3.6  | 7.99 | 7.99 | 3.54 | 3.49 |
| 75 | 0.17 | 0.32  | 4.2  | 1.8  | 7.99 | 7.99 | 3.53 | 3.48 |
| 80 | 0.23 | 0.51  | 3.3  | 1.0  | 7.99 | 8.00 | 3.54 | 3.52 |
| 88 | 0.83 | 1.20  | 1.2  | 0.6  | 7.99 | 7.90 | 3.51 | 3.42 |
| 94 | 2.23 | 2.73  | <0.5 | <0.5 | 7.94 | 7.81 | 3.53 | 3.47 |

TABLE 3

| Relative Humidity (%) | weight increase ratio (%) Ex. 2 | weight increase ratio (%) Ref Ex. 2 | Hardness (kg) Ex. 2 | Hardness (kg) Ref Ex. 2 | diameter (mm) Ex. 2 | diameter (mm) Ref Ex. 2 | thickness (mm) Ex. 2 | thickness (mm) Ref Ex. 2 |
|---|---|---|---|---|---|---|---|---|
| 0  | −0.06 | −0.15 | 5.0 | 4.1 | 7.97 | 7.97 | 3.52 | 3.52 |
| 31 | 0.00  | −0.10 | 4.6 | 4.8 | 7.98 | 7.97 | 3.50 | 3.52 |
| 40 | −0.02 | −0.13 | 4.8 | 4.2 | 7.97 | 7.98 | 3.52 | 3.52 |
| 53 | 0.05  | 0.07  | 4.0 | 2.8 | 7.97 | 7.97 | 3.49 | 3.51 |
| 75 | 0.09  | 0.25  | 3.9 | 2.0 | 7.97 | 7.97 | 3.50 | 3.53 |
| 80 | 0.19  | 0.42  | 3.0 | 0.8 | 7.97 | 7.97 | 3.50 | 3.53 |
| 88 | 0.53  | 0.89  | 1.0 | —   | 7.97 | 7.94 | 3.50 | 3.49 |
| 94 | 1.75  | 2.33  | —   | —   | 7.95 | 7.88 | 3.47 | 3.47 |

TABLE 4

| Relative Humidity (%) | weight increase ratio (%) Ex. 3 | weight increase ratio (%) Ref. Ex. 3 | Hardness (kg) Ex. 3 | Hardness (kg) Ref. Ex. 3 |
|---|---|---|---|---|
| 0  | 0.00 | −0.04 | 5.9 | 4.2 |
| 31 | 0.00 | 0.01  | 5.3 | 4.6 |
| 40 | 0.01 | 0.01  | 5.3 | 4.5 |
| 53 | 0.07 | 0.13  | 4.1 | 4.5 |
| 75 | 0.11 | 0.19  | 2.9 | 2.5 |
| 80 | 0.21 | 0.39  | 2.2 | 0.8 |
| 88 | 0.52 | 0.89  | 0.9 | —   |
| 94 | 2.00 | 2.29  | —   | —   |

As a result of the comparison/evaluation of Examples 1 to 3 with Reference Examples 1 to 3, the variations of the tablet weight, tablet hardness, tablet diameter, and tablet thickness of the quickly disintegrating tablet blended with polyvinyl alcohol as the binder were smaller than those of the quickly disintegrating tablet blended with polyvinyl pyrrolidone as the binder. That is, for the quickly disintegrating tablet blended with polyvinyl alcohol according to the present invention, as compared with the quickly disintegrating tablet blended with polyvinyl pyrrolidone, the tablet weight increase ratio was clearly reduced during the storage at a relative humidity of 75% or more, the variation of the tablet hardness was clearly reduced during the storage at a relative humidity of 53% or more, and the change of the tablet diameter was clearly reduced during the storage at a relative humidity of 88% or more. Moreover, the change of the thickness of the quickly disintegrating tablet blended with polyvinyl alcohol according to the present invention was remarkably reduced particularly in the storage condition of the relative humidity of 88% or more, when midodrine hydrochloride was used as the medicine (Example 1), as compared with the quickly disintegrating tablet blended with polyvinyl pyrrolidone (Reference Example 1).

It is clear that the quickly disintegrating tablet according to the present invention has small variations of the tablet weight, tablet hardness, tablet diameter and tablet thickness, and has satisfactory physical properties of the quickly disintegrating tablet during the storage under the humidifying condition.

Satisfactory Chemical Stability of Medicine Contained in Tablet According to the Present Invention The "quickly disintegrating tablet of famotidine blended with the saccharide and polyvinyl alcohol as the binder" obtained in Example 3 was stored together with Reference Example 3 (the quickly disintegrating tablet of famotidine blended with the saccharide and polyvinyl pyrrolidone as the binder) at 45° C., 25° C. and relative humidity of 75% and under an irradiation (1000 Lux) condition for three months, and the content stabilities of famotidine contained in the tablets and the stabilities of tablet appearances were compared/evaluated.

The famotidine content stability in the tablet was evaluated by using a tablet stored in a cold place as a reference and obtaining a residual ratio of the famotidine content, and the stability of the tablet appearance was visually evaluated using the tablet stored in the cold place as the reference. Additionally, the famotidine content was measured with an ultraviolet absorptiometer (measurement wavelength=266 nm) by a high-speed liquid chromatography method.

The result of the chemical stability evaluation of famotidine contained in the quickly disintegrating tablet is shown in Table 5.

TABLE 5

| Storage conditions: (stored for 3 months) | Ex. 3 famotidine content (%) | Ex. 3 appearance | Ref. Ex. 3 famotidine content (%) | Ref. Ex. 3 appearance |
|---|---|---|---|---|
| cold place | 100.0 | no change | 100.0 | no change |
| 45° C. | 100.0 | no change | 99.3 | no change |
| 25° C., R.H. 75% | 100.1 | no change | 99.4 | no change |
| irradiation (1000 Lux) | 99.7 | no change | 98.8 | colored (yellow) |

As the result of comparison/evaluation of Example 3 with Reference Example 3, the famotidine-containing quickly disintegrating tablet blended with polyvinyl alcohol as the binder according to the present invention had a larger content residual ratio than Reference Example 3 (the famotidine-containing quickly disintegrating tablet blended with polyvinyl pyrrolidone as the binder) even under any storage condition, and was stable without any change recognized in the tablet appearance.

Particularly, under the irradiation (1000 Lux) condition, the famotidine content residual ratio of Reference Example 3 (the famotidine-containing quickly disintegrating tablet blended with polyvinyl pyrrolidone as the binder) dropped to 98.8%, and a yellow-colored change was recognized also in the appearance of the tablet on an exposure side. On the other hand, in Example 3 according to the present invention (the famotidine-containing quickly disintegrating tablet blended with polyvinyl alcohol as the binder), the change was hardly recognized in both the content residual ratio and the tablet appearance change, and the tablet was stable.

It is clear that the quickly disintegrating tablet according to the present invention has a satisfactory chemical stability of the contained medicine (famotidine).

EXAMPLES

The present invention will be described hereinafter in more detail by way of Examples, but the present invention is not limited by them.

Example 1

20 g of midodrine hydrochloride and 1717.75 g of mannitol were sufficiently mixed in a mixer. To the mixture was added an aqueous ethanol solution with 12.25 g of polyvinyl alcohol dissolved in 245 g of 55% ethanol solution (prepared by stirring and dispersing 12.25 g of polyvinyl alcohol in pure water, dissolving while heating under stirring in a water bath at 80-90° C., cooling the solution, and then adding ethanol thereto), followed by kneading for about five minutes. The resulting kneaded wet powder was subjected to a compression-molding at a tableting pressure of 30 kg/cm$^2$ by a method mentioned in JP-A 8-19589 (the kneaded mixture was filled in a mold for the tablet molding of the pelletizer and at least one surface of the web powder in the above-mentioned mold was molded into a tablet by a metal mold for the molding via an adhesion preventing film), and then dried at 60° C. for 3 hours, to manufacture the tablet containing 2 mg of midodrine hydrochloride in one tablet of 175 mg.

The hardness of the tablet was about 5 kg, and the disintegration time in pure water was within 15 second.

Example 2

2.5 g of brotizolam and 1735.25 g of mannitol were sufficiently mixed in a mixer. To the mixture was added an aqueous ethanol solution with 12.25 g of polyvinyl alcohol dissolved in 245 g of 55% ethanol solution, followed by kneading for about five minutes. The resulting kneaded wet powder was subjected to a compression-molding at a tableting pressure of 30 kg/cm$^2$ by a method mentioned in JP-A 8-19589 (the kneaded mixture was filled in a mold for the tablet molding of the pelletizer and at least one surface of the wet powder in the above-mentioned mold was molded into a tablet by a metal mold for the molding via an adhesion preventing film), and then dried at 60° C. for 3 hours, to manufacture the tablet containing 0.25 mg of brotizolam in one tablet of 175 mg.

The hardness of the tablet was about 5 kg, and the disintegration time in pure water was within 15 seconds.

Example 3

200 g of famotidine and 1885.3 g of mannitol were sufficiently mixed in a mixer. To the mixture was added an aqueous ethanol solution with 14.7 g of polyvinyl alcohol dissolved in 249 g of 55% ethanol solution, followed by kneading for about five minutes. The resulting kneaded wet powder was subjected to a compression-molding at a tableting pressure of 28 kg/cm$^2$ by a method mentioned in JP-A 8-19589 (the kneaded mixture was filled in a mold for the tablet molding of the pelletizer and at least one surface of the wet powder in the above-mentioned mold was molded into a tablet by a metal mold for the molding via an adhesion preventing film), and then dried at 60° C. for 3 hours, to manufacture the tablet containing 20 mg of famotidine in one tablet of 210 mg.

The hardness of the tablet was about 5 kg, and the disintegration time in pure water was within 15 seconds.

Example 4

200 g of famotidine, 1782 g of lactose and 4 g of l-menthol were sufficiently mixed in a mixer. To the mixture was added an aqueous ethanol solution with 14 g of polyvinyl alcohol dissolved in 300 g of 55% ethanol solution, followed by kneading for about five minutes. The resulting kneaded wet powder was subjected to a compression-molding at a tableting pressure of 28 kg/cm$^2$ by a method mentioned in JP-A 8-19589 (the kneaded mixture was filled in a mold for the tablet molding of the pelletizer and at least one surface of the web powder in the above-mentioned mold was molded into a tablet by a metal mold for the molding via an adhesion preventing film), and then dried at 60° C. for 3 hours, to manufacture the tablet containing 20 mg of famotidine in one tablet of 200 mg.

The hardness of the tablet was about 5 kg, and the time for disintegration in pure water was within 15 seconds.

Example 5

400 g of donepezil hydrochloride, 2000 g of mannitol, 100 g of light silicic anhydride and 300 g of carrageenan were well mixed in a mixer. Pure water was added thereto, and the mixture was granulated, dried and sized, to give the granule (A).

Subsequently, 700 g of the granule (A) and 2080 g of mannitol were sufficiently mixed in the mixer, an aqueous ethanol solution with 20 g of polyvinyl alcohol dissolved in 336 g of 25% ethanol solution was added thereto, followed by kneading for about five minutes. The resulting kneaded wet powder was subjected to a compression-molding by a method mentioned in JP-A 8-19589 (the kneaded mixture was filled in a mold for the tablet molding of the pelletizer and at least one surface of the wet powder in the above-mentioned mold was molded into a tablet by a metal mold for the molding via an adhesion preventing film), and then dried at 50-90° C. for several hours, to manufacture the tablet containing 10 mg of donepezil hydrochloride in one tablet of 280 mg.

The hardness of the tablet was about 5 kg, and the time for disintegration in the pure water was within 15 seconds.

The invention claimed is:

1. A method for producing a compressed quickly disintegrating tablet, said method comprising the steps of:
    mixing donepezil hydrochloride with mannitol;
    kneading the mixture with water including polyvinyl alcohol dissolved therein or with an aqueous organic solvent;
    subjecting the kneaded mixture to a compression-molding; and
    producing said quickly disintegrating and compressed tablet comprising donepezil hydrochloride, mannitol and polyvinyl alcohol, wherein said mannitol is mixed in an amount of 0.8 part by weight or more to 1 part by weight of said tablet, and said polyvinyl alcohol is mixed in an amount of 0.001 to 0.05 part by weight to 1 part by weight of said tablet.

2. The method for producing a compressed quickly disintegrating tablet of claim 1, further comprising:
    subjecting the kneaded mixture to the compression-molding via a film.

3. The method for producing a compressed quickly disintegrating tablet of claim 1, further comprising the step of filling a mold with the kneaded mixture after the step of the kneading the mixture with water or the aqueous organic solvent.

* * * * *